United States Patent [19]
Chaisson et al.

[11] Patent Number: 6,086,548
[45] Date of Patent: Jul. 11, 2000

[54] CAROTID ARTERY ANGIOLASTY GUIDING SYSTEM AND METHOD

[76] Inventors: Gary A. Chaisson, 215 Angelle Ct.; Craig M. Walker, 312 Keystone Loop, both of Houma, La. 70360

[21] Appl. No.: 09/255,836

[22] Filed: Feb. 23, 1999

Related U.S. Application Data

[60] Provisional application No. 60/004,942, Oct. 4, 1996.

[51] Int. Cl.<sup>7</sup> ..................................................... A61B 5/00
[52] U.S. Cl. ........................... 600/585; 604/95; 604/96; 604/280
[58] Field of Search .................................. 600/585, 433, 600/435; 604/95, 96, 280, 281

[56] References Cited

U.S. PATENT DOCUMENTS

| | | |
|---|---|---|
| 4,581,017 | 4/1986 | Sahota . |
| 4,781,682 | 11/1988 | Patel . |
| 4,884,573 | 12/1989 | Wijay et al. . |
| 4,886,067 | 12/1989 | Palermo . |
| 4,886,506 | 12/1989 | Lovgren et al. . |
| 5,203,776 | 4/1993 | Durfee . |
| 5,215,540 | 6/1993 | Anderhub . |
| 5,267,982 | 12/1993 | Sylvanowicz . |
| 5,299,574 | 4/1994 | Bower . |
| 5,348,545 | 9/1994 | Shani et al. . |
| 5,389,090 | 2/1995 | Fischell et al. . |
| 5,401,258 | 3/1995 | Voda . |
| 5,447,503 | 9/1995 | Miller . |
| 5,449,362 | 9/1995 | Chaisson et al. . |
| 5,680,873 | 10/1997 | Berg et al. . |
| 5,725,512 | 3/1998 | Swartz et al. . |
| 5,833,650 | 11/1998 | Imran ........................................ 604/53 |

*Primary Examiner*—Cary O'Connor
*Assistant Examiner*—Pamela L Wingood
*Attorney, Agent, or Firm*—Garvey, Smith, Nehrbass & Doody, L.L.C.

[57] ABSTRACT

A method and apparatus for performing an angioplasty of a patient's carotid artery includes a placement of a first elongated positioning catheter having a lumen and proximal and distal end portions within a patient's body so that the distal end portion of the positioning catheter occupies a position within the patient's aorta next to the patient's selected carotid artery. The distal end portion of the positioning catheter is curved with a radius of curvature of about 2 cm, for example, and provides a soft distal tip. Using fluoroscopy, a user can manipulate, rotate, and position the positioning catheter until the distal tip enters the carotid artery. A guide wire is then advanced through the lumen of the positioning catheter until the free end portion of the wire reaches the distal tip of the positioning catheter and enters the selected carotid artery. A second catheter is advanced over the positioning catheter, the second catheter being a guiding catheter having a distal end portion. The distal end portion of the guiding catheter is shaped to provide two curved sections or bends. The distal end portion of the guiding catheter includes a central section and a pair of opposed sections. The two bends or curved portions form respective connections between the central section and each of the opposed sections.

17 Claims, 5 Drawing Sheets

CAROTID ARTERY ANGIOLASTY GUIDING SYSTEM AND METHOD

Priority of U.S. Provisional Patent Application Ser. No. 60/004,942, filed Oct. 4, 1996, is hereby claimed. That application is hereby incorporated by reference.

BACKGROUND OF THE INVENTION

1. Field of the Invention

The present invention relates to cardiac catheter devices and more particularly to an improved method and apparatus for eliminating a constriction or narrowing of a patient's carotid artery.

2. General Background

Atherosclerotic stenosis of the extracranial carotid arteries (the arteries on each side of the neck that supply blood to the head and neck) causes a significant portion of the 500,000 strokes that occur each year in the U.S. The superiority of carotid endarterectomy over medical management has been clearly demonstrated in symptomatic patients. Recently, the Asymptomatic Carotid Atherosclerosis Study showed a marked reduction in the incidence of stroke following carotid endarterectomy in asymptomatic carotid stenosis of >60%. These studies have provided clear evidence of the benefit of revascularization of the diseased extracranial carotid artery. Carotid endarterectomy is performed now surgically through an artery in the patient's neck.

Surgery, however, has several limitations. In patients with angina, morbidity and mortality rates as high as 18% have been reported. Endarterectomy is generally confined to the cervical portion of the carotid artery. Cranial nerve palsies occur in 7.6% to 27% of patients. Restenosis after endarterectomy appears to occur in 10% to 19% of patients.

Percutaneous techniques have the potential for being safer, less traumatic, more cost effective, usable in patients at high surgical risk, and are not limited to the cervical carotid artery. These potential benefits, however, have yet to be realized for the general population of patients with carotid disease even though percutaneous carotid balloon angioplasty (PCBA) was first performed in 1980. Angioplasty is a procedure for alleviating blockage of an artery in which a balloon tipped catheter is threaded into an artery to a point of obstruction and inflated to push the vessel open.

Surgeons are presently using catheters designed for coronary angioplasty and peripheral angioplasty. Thus, there exists a need for a catheter system specifically designed for carotid arteries.

U.S. Pat. No. 5,449,362 and prior applications, PCT Application no. PCT/US95/06205, and all patents mentioned herein and therein, are incorporated herein by reference.

SUMMARY OF THE INVENTION

The present invention provides a method of performing angioplasty on a patient's carotid artery. The method includes the initial placement of a positioning catheter within a patient's body so that the distal end of the positioning catheter occupies a position within the patient's aorta next to a selected carotid artery.

A user (Cardiologist, assistant, or technician, etc.) rotates the distal end of the positioning catheter to position a curved end portion and distal tip of the positioning catheter at the intersection of the carotid artery and the aorta. The user then positions the distal tip into the carotid artery.

A guide wire is then advanced through the lumen of the positioning catheter until the free end of the wire reaches the distal tip of the positioning catheter and the carotid artery.

A second (guiding) catheter having a lumen is then advanced over the positioning catheter. The second catheter has proximal and distal end portions and a lumen that receives the first (positioning) catheter.

The distal end portion of the second catheter includes three sections, including a central section and a pair of opposed sections with two bends forming the connections respectively between the central section and the opposed sections. The bends of the guiding catheter position the distal end at the patient's carotid artery during use. One of the bends is much larger in curvature and it tracks the patient's aorta during use at a location spaced away from the target carotid artery.

The present invention also provides a catheter apparatus for dilating a stenosis in a patient's carotid artery. The apparatus includes a first, positioning catheter having proximal and distal end portions and a lumen. The distal end portion of the positioning catheter is curved to provide a tip portion that enables the user to access a selected one of the patient's carotid arteries when the positioning catheter occupies the patient's aorta.

The apparatus further includes a guide wire that fits the lumen of the positioning catheter. The guide wire provides a free end portion that travels through the lumen of the positioning catheter to the distal end portion thereof so that the guide wire can enter the patient's carotid artery at the distal end of the positioning catheter.

A second catheter (guiding catheter) has proximal and distal end portions and a lumen that enables the guiding catheter to advance over the positioning catheter during use.

The distal end portion of the guiding catheter has two curved sections including a first curved section that is closest to the distal tip and a second curved section that has less curvature than the first curved section. The second curved section is spaced away from the distal tip and first curved section.

The distal end portion of the guiding catheter includes a central section and a pair of opposed sections positioned on opposite sides of the central section.

The central section forms an angle with each of the opposed sections to define the first and second curved sections, including a first obtuse angle and a second much smaller angle, preferably about 90°. The obtuse angle is preferably about 130°.

During use, the smaller 90° angle bend is positioned adjacent the carotid artery to be treated. The obtuse angle tracks the patient's aorta at a location spaced away from the carotid artery.

The apparatus of the present invention can include a third catheter with a reinforcing section that fits over the curved portions of the guiding catheter during use. However, the reinforcing section can also have correspondingly shaped curved portions to fit the curved sections of the guiding catheter. Thus, the reinforcing section of the third catheter can be used to maintain the curvatures of the guiding catheter when stiff objects such as a stent are routed through/advanced through the lumen of the guiding catheter.

In order to insert a stent, an instrument, a balloon, an atherectomy device, or a device that will inject a drug, the wire and positioning catheter are first removed. The user can then deploy selected instruments, stents, drugs, balloons, atherectomy devices, etc. via the lumen of the third reinforcing catheter or the lumen of the guiding catheter.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Parts List:
- 20 guide wire
- 30 carotid artery positioning catheter
- 31 distal end of the positioning catheter 30
- 40 carotid guiding catheter
- 41 primary curve of carotid guiding catheter 40
- 41A–41H primary curve of carotid guiding catheters 40A–40H
- 42 distal end of carotid guiding catheter 40
- 43 secondary curve of carotid guiding catheter 40
- 43A–43H secondary curve of carotid guiding catheters 40A–40H
- 50 carotid reinforcing sheath (guide sheath)
- 51 distal end of carotid reinforcing sheath 50
- 52 reinforced segment of carotid reinforcing sheath 50
- 60 commercially available femoral sheath to be located in femoral artery
- 70 pressure tubing system
- 80 anchoring device (valve)
- 90 Y-connector
- 110 balloon catheter
- A patient's aortic arch
- C right common carotid artery
- L left common carotid artery
- S subclavian artery
- V left vertebral The present invention comprises a catheter system for facilitating percutaneous angioplasty of the carotid artery and a method of using the catheter system in performing percutaneous angioplasty of the carotid artery. The carotid arteries are those arteries on the sides of the neck that supply blood to the head and neck.

Figure 1:
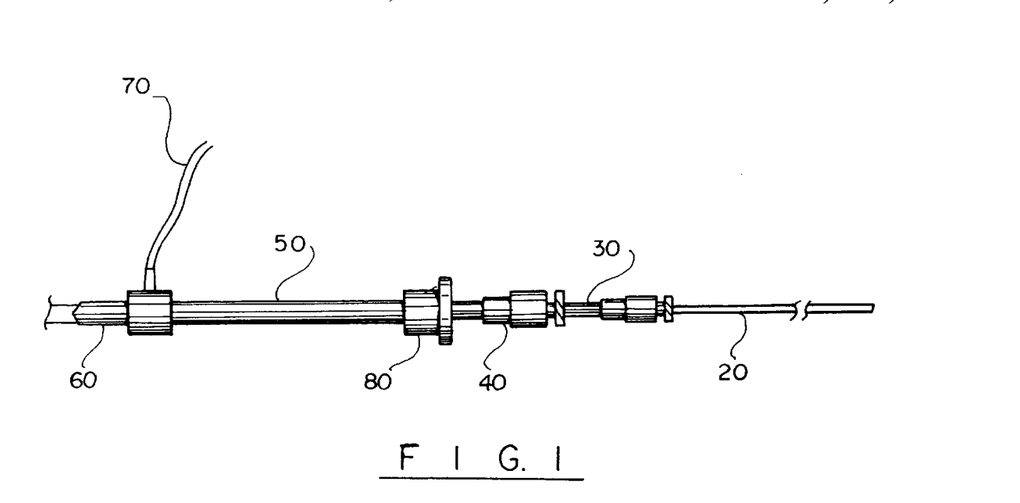
FIG. 1 is a plan view of the preferred embodiment of the apparatus of the present invention shown in use with a pressure tubing system.
Figure 2:
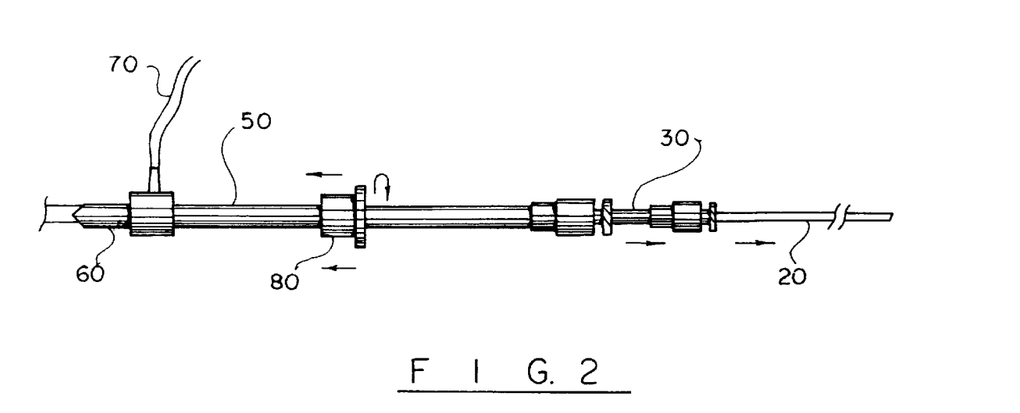
FIG. 2 is plan view of the preferred embodiment of the apparatus of the present invention showing advancement of the guide sheath over the carotid guiding catheter to provided added support around the aortic arch.
Figure 3:
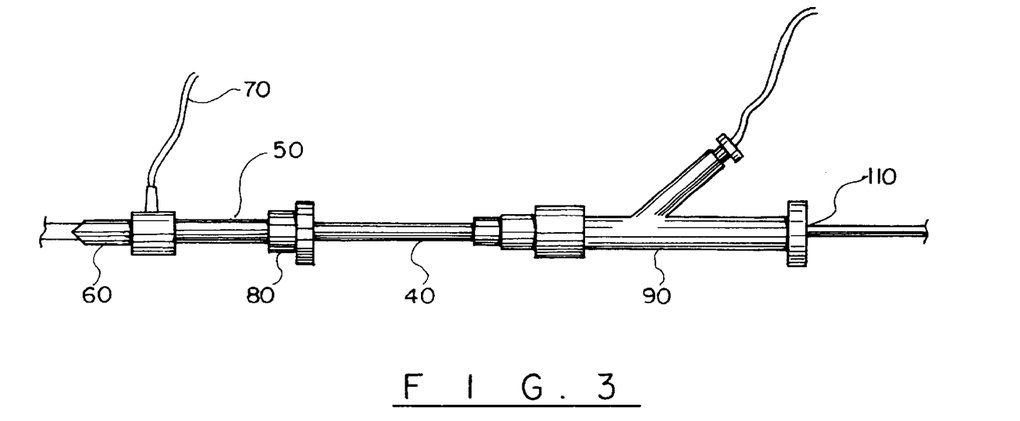
FIG. 3 is a plan view of the preferred embodiment of the apparatus of the present invention showing its use with a Y-type connector and balloon catheter.

In FIGS. 1–4, the catheter system 10 includes a guide wire 20, a carotid positioning catheter 30, a carotid guiding catheter 40, and a carotid reinforcing sheath 50. In practice, an incision is made in a femoral artery in the patient. As shown in FIGS. 1–3, commercially available femoral sheath 60 (having a pressure tubing system 70) is placed through the incision into the femoral artery. The positioning catheter 30 is placed inside the guiding catheter 40, which in turn is placed within the reinforcing sheath 50. The guide wire 20 is placed inside the positioning catheter 30.

In FIGS. 1–3, only proximal portions of the guide wire 20, sheath 50, and catheters 30 and 40 are shown. Only distal portions of the guide wire 20, sheath 50, and catheters 30 and 40 are shown in FIGS. 5–12.

Figures 4, 5, 6, 8:
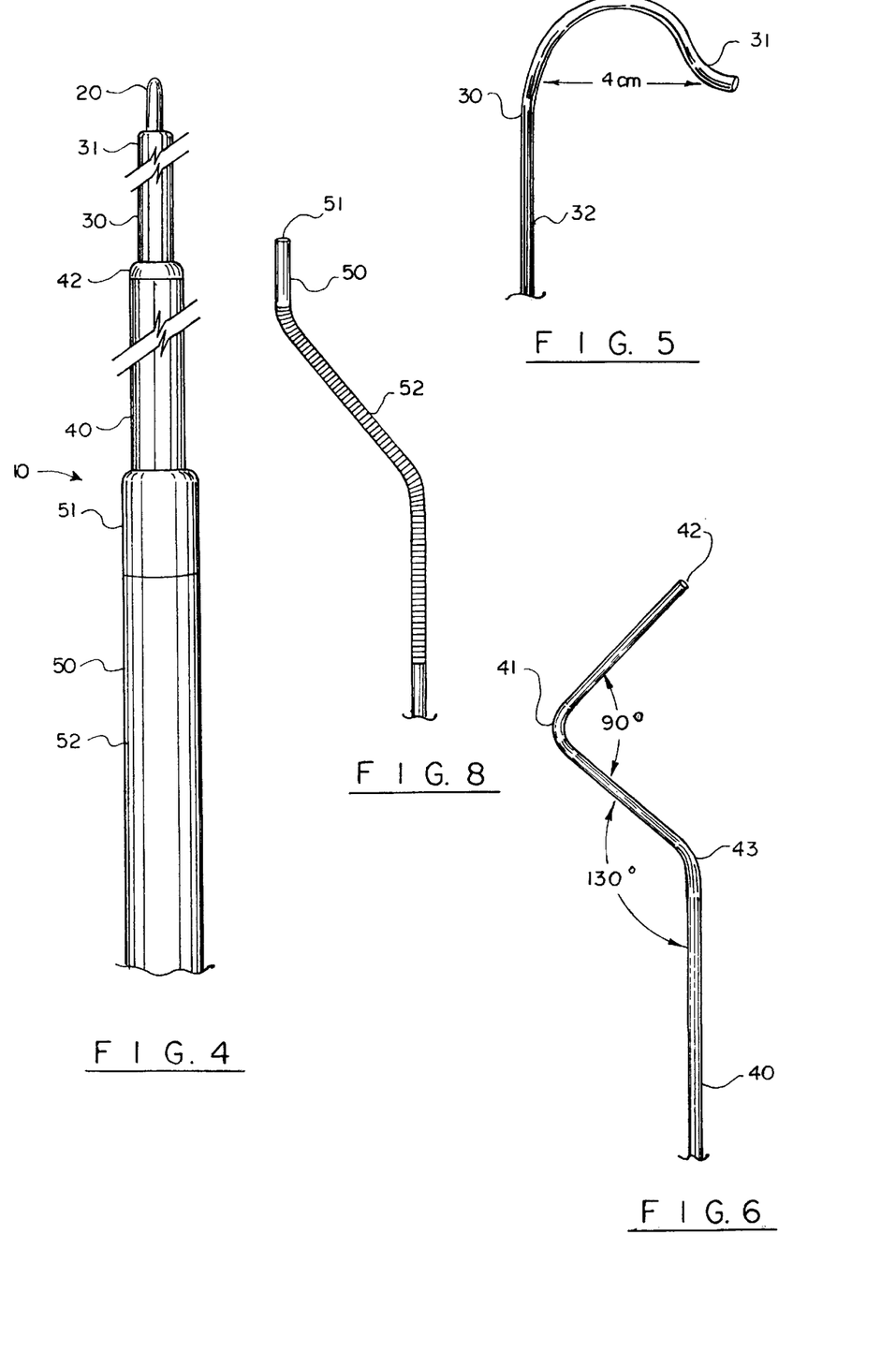
FIG. 4 is a plan view of the preferred embodiment of the apparatus of the present invention.
FIG. 5 is a partial schematic view of the positioning catheter portion of the preferred embodiment of the apparatus of the present invention.
FIG. 6 is a fragmentary view of the preferred embodiment of the apparatus of the present invention illustrating the carotid guiding catheter.
FIG. 8 is a schematic view illustrating the reinforcing sheath portion of the preferred embodiment of the apparatus of the present invention.
Figure 9:
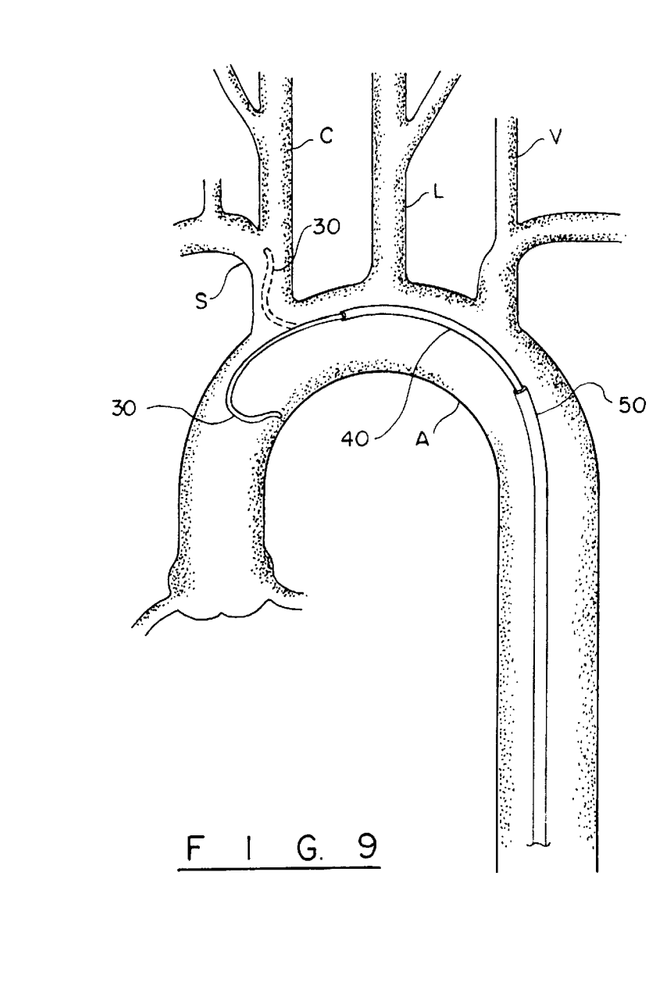
FIG. 9 is a schematic view of a patient's aortic arch and the adjacent subclavian artery, and carotid artery, showing the first method step of the present invention in placement of the positioning catheter.
Figure 10:
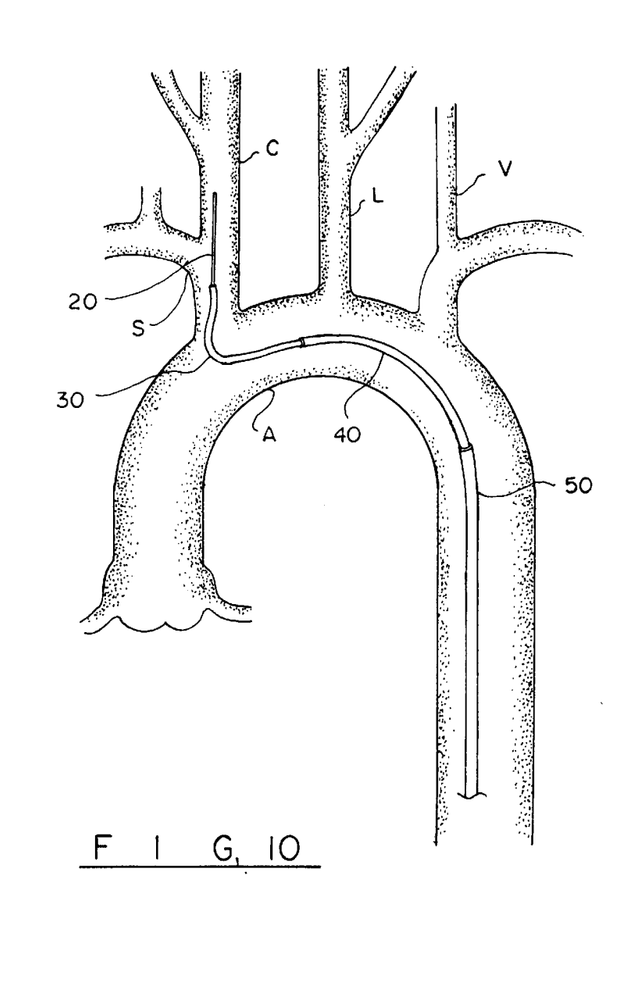
FIG. 10 illustrates the second method step of the method of the present invention.
Figure 11:
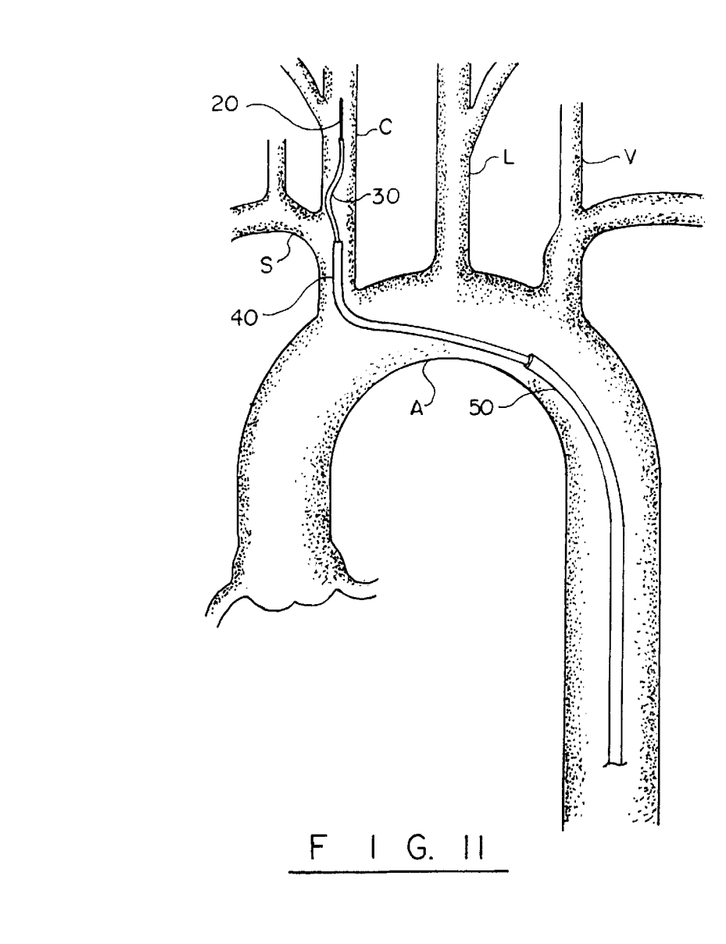
FIG. 11 illustrates the third method step of the method of the present invention.
Figure 12:
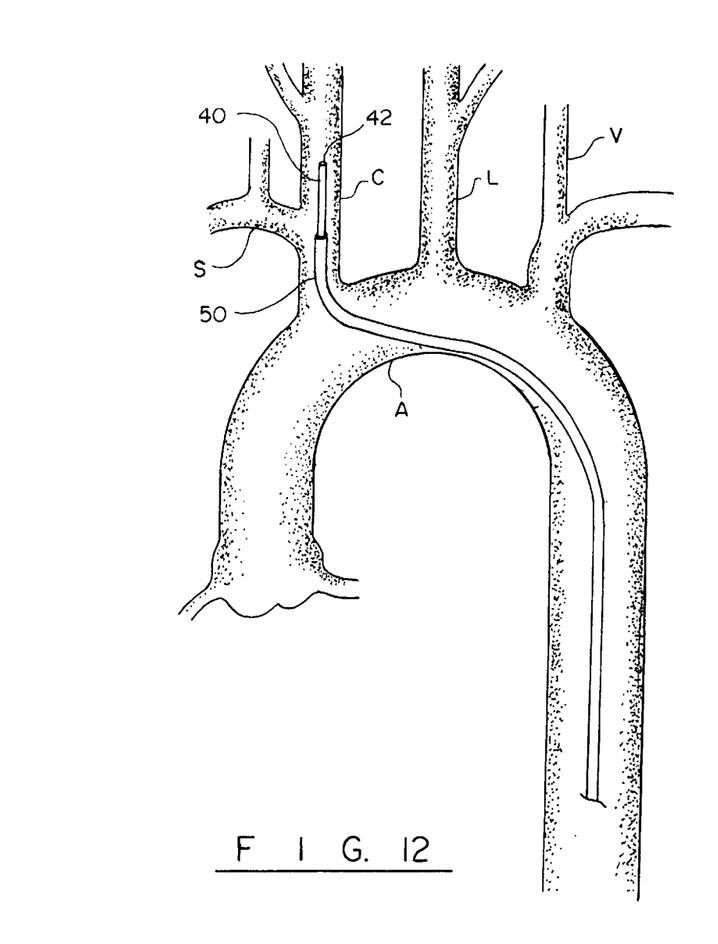
FIG. 12 illustrates the fourth method step of the method of the present invention.

The distal end 31 of the positioning catheter 30 is first advanced to the patient's aortic arch A (see FIGS. 5 and 9). When the distal end 31 of the positioning catheter 30 is adjacent the right subclavian artery S (see FIG. 9), the free distal end 31 of positioning catheter 30 is manipulated and rotated (using fluoroscopy) to enter the right subclavian artery (see FIG. 10). As shown in FIG. 5, the free distal end 31 is connected to main portion 32 with a U-shaped portion having a radius of curvature of about 2 cm.

The carotid artery positioning catheter 30 has a relatively straight main longitudinal portion 32 and has a distal tip portion which is curved and has a distal tip 31 which extends approximately perpendicularly about 4 cm from its main longitudinal portion 32, as shown in FIG. 5.

In the carotid guiding catheter 40 (see FIG. 6), the primary curve 41 is preferably 3–8 cm from the distal end. There is a, for example, 3 mm soft tip at the distal end 42. The primary curve 41 is preferably about 90 degrees. The secondary curve 43 is 5–10 cm from the primary curve 41 and is preferably about 130 degrees. The carotid guiding catheter 40 is, for example, 90–110 cm long and 8–11 Fr.

The guide wire 20 is then advanced through the lumen of positioning catheter 30 into the subclavian artery S (see FIG. 10) until it reaches the target area in the carotid artery C. The guiding catheter 40 is advanced along the positioning catheter 30 and guide wire 20 (see FIG. 11) until its distal free end 42 is adjacent the distal end of the guide wire 20.

The reinforcing sheath 50 is then advanced along the guiding catheter 40 until its distal end 51 is adjacent the distal end 42 of the guiding catheter 40 (see FIG. 12), to provide added support around the aortic arch A.

The anchoring device 80 (see FIGS. 1–3) is then tightened to secure the reinforcing sheath 50 to the guiding catheter 40. Once this occurs, the guide wire 20 and positioning catheter 30 are removed, leaving only the guiding catheter 40 and the reinforcing sheath 50 in the patient (see FIG. 12).

Appropriate medicine can be administered, and appropriate procedures can be performed, through the guiding catheter 40. For example, a Y-connector 90 can be attached to the guiding catheter 40 (see FIG. 3) to allow a balloon catheter 110 to be inserted into the carotid artery.

Figure 7:
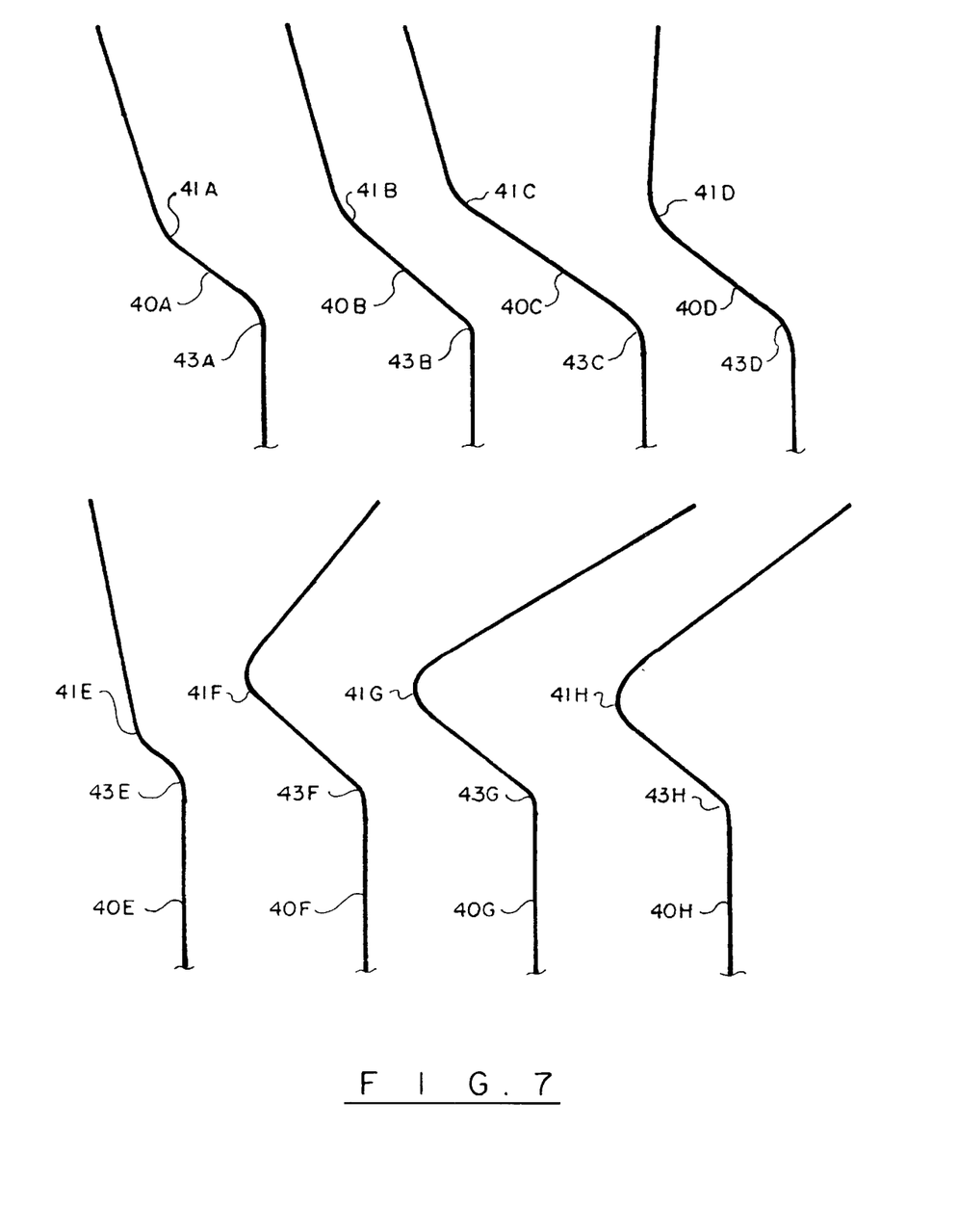
FIG. 7 is an illustration of various carotid guiding catheter shapes for the preferred embodiment of the apparatus of the present invention.

FIG. 7 shows various shapes for the primary curve (41A–41H) and secondary curve (43A–43H) of the carotid guiding catheter (catheters 40A–40H). In FIG. 7, the primary curve (41A–41H) is about 70 degrees to about 150 degrees. The angle of the primary curve of the carotid guiding catheter is dependent on the anatomy of the patient. One chooses an angle which is appropriate for the anatomy of a patient (an angle which makes it possible and relativley easy to successfully manuever the tip selectively into the right or left common carotid artery).

In FIG. 7, the secondary curve (43A–43H) of the carotid guiding catheter (catheters 40A–40H) is about 130 degrees. The secondary curve of the carotid guiding catheter is preferably about 95 degrees to about 165 degrees. More preferably, the secondary curve of the carotid guiding catheter is about 100 degrees to about 160 degrees. Most preferably, the secondary curve of the carotid guiding catheter is about 120 degrees to about 140 degrees.

The carotid reinforcing sheath 50 (see FIG. 4) has a distal end 51 which has a soft tip which can be, for example, about 3 cm–5 cm (and preferably 3 cm) long. There is a 10–20 cm long reinforced segment 52 of the sheath 50 which extends across the primary and secondary bends 41 and 43 of the carotid guiding catheter 40.

The use of the carotid reinforcing sheath 50 allows the guide wire 20 to be sufficiently flexible that it causes very little, if any, trauma as it is advanced toward the target area in the carotid artery C. Were it not for the carotid reinforcing sheath 50, the guide wire 20 would need to be strong enough (stiff enough) to provide structural support for the carotid guiding catheter 40 and to prevent the carotid guiding catheter 40 from kinking, or the carotid guiding catheter 40 itself would need to be made stiffer.

The length of the reinforcing sheath 50 can be, for example, 80–100 cm (or even longer if used on a tall person).

All of the catheters 20, 30, 40 can be manufactured of polyethylene, polyurethane, or other suitable polymers. They can be coated with a lubricous material such as polytetrafluoroethylene (PTFE) or hydrophilic polymer.

The reinforced segments of the guide sheath 50 or guiding catheter 40 can be reinforced with a metal such as Nitinal brand metal, stainless steel, or other inert metal or polymer. It may be fabricated from memory alloys or bimetal thermocouples, for example.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A method of performing angioplasty on a patient's selected carotid artery comprising the steps of;

a) placing an elongated positioning catheter having a lumen and proximal and distal end portions within a patient's body so that the distal end of the positioning catheter occupies a position within the patient's aorta next to the patient's selected carotid artery;

b) wherein in step "a" the distal end of the positioning catheter has a curved portion and a distal tip;

c) rotating and positioning the catheter until the distal tip enters the carotid artery;

d) advancing a guide wire having a free end portion through the lumen of the positioning catheter from the proximal end to the distal end until the free end portion of the wire reaches the distal tip of the positioning catheter and the selected carotid artery;

e) advancing a second catheter with a lumen over the positioning catheter, the second catheter having proximal and distal end portions, the distal end portion including a central section and a pair of opposed sections, with two bends forming respective connections between the central section and the opposed sections, the first bend having a smaller curvature and the second bend having a larger curvature; and f) wherein in step "e" the second curvature includes the central section and an opposed section that together form an obtuse angle.

2. The method of claim 1 further comprising the step "g" of advancing a third catheter having proximal and distal end portions over the second catheter until the distal end portion of the third catheter is positioned next to the distal end portion of the second catheter.

3. The method of claim 1 wherein step "e" comprises advancing a second catheter with a lumen over the positioning catheter, the second catheter having a distal end portion that includes two bends including a first bend in between two catheter sections that form an angle of about ninety degrees and a second bend in between two catheter sections that form an angle of about one hundred thirty degrees.

4. The method of claim 1 wherein step "e" comprises advancing a second catheter with a lumen over the positioning catheter, the second catheter having proximal, central and distal sections and two bends including a first bend defined by a first angle of about ninety degrees formed by the central and distal sections and a second bend defined by an second angle formed by the central and proximal sections.

5. The method of claim 1 wherein step "e" comprises advancing a second catheter with a lumen over the positioning catheter, the second catheter having proximal, central and distal sections and two bends including a first bend defined by a first angle formed by the central and distal sections and a second bend defined by an second angle formed by the central and proximal sections, wherein the second angle is substantially larger than the first angle.

6. The method of claim 1 wherein the third catheter has a reinforced stiffened section and step "g" comprises advancing the third catheter over the second catheter until the distal end portion of the third catheter is positioned next to the distal end portion of the second catheter, and further comprising the step "h" of generally aligning the reinforced stiffened section with the two bends of the second catheter.

7. The method of claim 1 wherein the third catheter has a reinforced stiffened section with two bends and step "g" comprises advancing the third catheter over the second catheter until the distal end portion of the third catheter is positioned next to the distal end portion of the second catheter, and further comprising the step "h" of generally aligning the two bends of the reinforced stiffened section with the two bends of the second catheter.

8. The method of claim 1 wherein the third catheter has a reinforced stiffened section and step "g" comprises advancing the third catheter over the second catheter until the distal end portion of the third catheter is positioned next to the distal end portion of the second catheter, and further comprising the step "h" of generally aligning the two bends of the reinforced stiffened section with the two bends of the second catheter, and wherein the combination of the second and third catheters define a catheter assembly with two bends.

9. The method of claim 1 further comprising the step of withdrawing the wire from the lumen of the positioning catheter.

10. The method of claim 1 further comprising the step of withdrawing the wire and the positioning catheter from the lumen of the guiding catheter.

11. The method of claim 1 further comprising the step of positioning the first bend near the intersection of the patient's aorta and a selected subclavian artery.

12. The method of claim 1 further comprising the step of positioning the first bend near the intersection of the patient's aorta and a selected one of the patient's carotid arteries.

13. The method of claim 1 further comprising the step of positioning the second bend in the patient's aorta at a position spaced away from the carotid arteries.

14. The method of claim 1 further comprising the step of advancing an instrument through the lumen of one of the catheters until the instrument reaches the carotid artery.

15. The method of claim 1 further comprising the step of advancing a stent through the lumen of one of the catheters until the stent reaches the carotid artery.

16. The method of claim 14 further comprising the step of dilating the carotid artery at a stenosis.

17. The method of claim 15 further comprising the step of dilating the carotid artery at a stenosis.

* * * * *

UNITED STATES PATENT AND TRADEMARK OFFICE
CERTIFICATE OF CORRECTION

PATENT NO. : 6,086,548
DATED : July 11, 2000
INVENTOR(S) : Chaisson et al.

It is certified that error appears in the above-identified patent and that said Letters Patent is hereby corrected as shown below:

Title page, section [54], delete "ANGIOLASTY" and insert --ANGIOPLASTY--.

Title page, setion [60], delete Provisional application No. 60/004,942, Oct. 4,1996." and insert -- Divisional of Ser. No. 720,946, Oct. 4, 1996, Pat. No. 5,891,057, which claims benefit of Provisional application No. 60/004,942, Oct. 4, 1995.--.

In column 1, line 1, delete "ANGIOLASTY" and insert --ANGIOPLASTY--

In column 1, delete lines 4-6 and insert
--This is a divisional of application Ser. No. 720,946, filed Oct. 4, 1996, Pat. No. 5,891,057, which claims benefit of U.S. Provisional Patent Application Ser. No.60,004,942, filed Oct. 4, 1995. These applications are hereby incorporated by reference.--.

Signed and Sealed this

Fifth Day of June, 2001

Attest:

NICHOLAS P. GODICI

*Attesting Officer*

*Acting Director of the United States Patent and Trademark Office*